US010265421B2

(12) United States Patent
Jensen et al.

(10) Patent No.: US 10,265,421 B2
(45) Date of Patent: Apr. 23, 2019

(54) HYPERPOLARIZED ESTERS AS METABOLIC MARKERS IN MR

(71) Applicant: BRACCO IMAGING S.P.A., Milan (IT)

(72) Inventors: Pernille Rose Jensen, Vaerlose (DK); Lerche H. Mathilde, Frederiksberg C (DK); Magnus Karlsson, Malmö (SE); Claudia Cabella, Pecco (IT); Sonia Colombo Serra, Vigliano Biellese (IT); Luigi Miragoli, Dovera (IT); Luca Venturi, Piacenza (IT); Fabio Tedoldi, Marzano (IT)

(73) Assignee: BRACCO IMAGING S.P.A., Milan (IT)

( * ) Notice: Subject to any disclaimer, the term of this patent is extended or adjusted under 35 U.S.C. 154(b) by 358 days.

(21) Appl. No.: 14/764,568

(22) PCT Filed: Jan. 30, 2014

(86) PCT No.: PCT/EP2014/051760
§ 371 (c)(1),
(2) Date: Jul. 29, 2015

(87) PCT Pub. No.: WO2014/118258
PCT Pub. Date: Aug. 7, 2014

(65) Prior Publication Data
US 2015/0374854 A1    Dec. 31, 2015

(30) Foreign Application Priority Data

Jan. 31, 2013 (EP) ..................... 13153469

(51) Int. Cl.
*A61B 5/055*    (2006.01)
*A61K 49/10*    (2006.01)
*A61K 51/04*    (2006.01)

(52) U.S. Cl.
CPC .............. *A61K 49/10* (2013.01); *A61K 51/04* (2013.01)

(58) Field of Classification Search
None
See application file for complete search history.

(56) References Cited

U.S. PATENT DOCUMENTS

| 8,198,038 B2 | 6/2012 | Paik et al. | |
| 2010/0178249 A1 | 7/2010 | Brindle et al. | |
| 2011/0038802 A1 | 2/2011 | Hu et al. | |
| 2013/0096420 A1* | 4/2013 | Aime ..................... | A61K 49/10 600/420 |

FOREIGN PATENT DOCUMENTS

| EP | 2 052 273 B1 | 3/2012 |
| WO | 99/35508 A1 | 7/1999 |
| WO | 2006/011809 A1 | 2/2006 |
| WO | 2008/143519 A1 | 11/2008 |
| WO | 2009/077575 A1 | 6/2009 |
| WO | 2011/124672 A1 | 10/2011 |
| WO | 2011/138269 A1 | 11/2011 |
| WO | 2011/102773 A2 | 8/2012 |
| WO | 2013/006520 A1 | 1/2013 |

OTHER PUBLICATIONS

Park et al. (Neuor-Oncology 2010, 12, 133-144).*
Nelson (Proc. Intl. Soc. Mag. Reson. Med. 2011, 19, pp. 1-6).*
Sauer et al. (Cancer Res. 1983, 43, 3497-3503).*
Fenselau et al. (Cancer Res. 1975, 2315-2320).*
Brindle et al. (Mag. Reson. Med. 2011, 66, 505-519).*
Mayfield2018 p. 1-2.*
Hurd et al., "Metabolic imaging in the anesthetized rat brain using hyperpolarized [1-13C]-pyruvate and [1-13C] Ethyl pyruvate," Magn. Reson. Med. 2010; 63(5): 1137-1143.
Lobell et al., "Enzyme-assisted preparation of Pure Alkanedicarboxylic acids monoesters: chain-length dependence of porcine liver esterase (PLE)-catalysed hydrolyses," J . Chem. Soc. Perkin Trans. I, 1993, pp. 1713-1714.
Day S.E. et al., "Detecting tumor response to treatment using hyperpolarized 13C magnetic resonance imaging and spectroscopy," Nat Med 2007; 13:1382-1387.
European Search Report for European application No. 13153469.5, dated Jun. 18, 2013.
Gallagher F.A. et al.,"13C MR spectroscopy measurements of glutaminase activity in human hepatocellular carcinoma cells using hyperpolarized 13C-labeled glutamine," Magn Reson Med 2008; 60:253-257.
Gallagher F.A. et al., "Magnetic resonance imaging of pH in vivo using hyperpolarized 13C-labelled bicarbonate," Nature 2008; 453:940-943 and Full Methods available at www.nature.com/nature.
Gallagher F.A. et al., "Production of hyperpolarized [1,4-13C2]malate from [1,4-13C2]fumarate is a marker of cell necrosis and treatment response in tumors," Proc Natl Acad Sci USA 2009; 106:19801-19806.
Hu S. et al., "In vivo carbon-13 dynamic MRS and MRSI of normal and fasted rat liver with hyperpolarized 13C-pyruvate," Mol Imaging Biol 2009; 11:399-407.
Imai T. "Human Carboxylesterase Isozymes: Catalytic Properties and Rational Drug Design," Drug Metab. Pharmacokinet 2006; 21(3): 173-85.
Jansen et al., "CPT-11 in human colon cancer cell lines and xenografts: characterization of cellular sensitivity determinants," Int. J. Cancer 1997; 70:335-40.
Jensen P.R. et al., "Tissue-specific short chain fatty acid metabolism and slow metabolic recovery after ischemia from hyperpolarized NMR in vivo," J Biol Chem 2009; 284:36077-36082.

(Continued)

*Primary Examiner* — Michael G. Hartley
*Assistant Examiner* — Melissa J Perreira
(74) *Attorney, Agent, or Firm* — Vivicar Law, PLLC (57) ABSTRACT

The invention relates to a method of Magnetic Resonance (MR) detection, in particular $^{13}$C-MR detection, by using a diagnostic medium comprising a hyperpolarized ester, in particular ethyl acetoacetate. The method comprises the detection of the MR signal of a hyperpolarized $^{13}$C carboxylic ester and of its respective hyperpolarized metabolite.

10 Claims, 8 Drawing Sheets

(56) References Cited

OTHER PUBLICATIONS

Jensen P.R. et al., "Hyperpolarized 1,3-13C2-Ethylacetoacetate is a novel diagnostic metabolic marker of liver cancer," 4th international DNP symposium, Copenhagen, Denmark, Aug. 28, 2013, p. 101, XP055119258.

Karlsson M. et al., "Imaging of branched chain amino acid metabolism in tumors with hyperpolarized 13C ketoisocaproate," Int J Cancer 2010; 127:729-736.

Kennedy B.W.C. et al., "Detection of hyperpolarized 13C labelled ketone bodies in vivo," Proceedings of the International Society for Magnetic Resonance in Medicine 2012; 20:4326, XP040626747.

Liewald et al, "Intracellular pH, esterase activity and DNA measurements of human lung carcinomas by flow cytometry," Cytometry 1990; 11: 341-48.

Merritt et al., "Hyperpolarized 13C allows a direct measure of flux through a single enzyme-catalyzed step by NMR," Proc Natl Acad Sci USA 2007; 104:19773-19777.

Na, K. et al., "Human plasma carboxylesterase 1, a novel serologic biomarker candidate for hepatocellular carcinoma," Proteomics 2009; 9: 3989-99.

PCT Search Report and Written Opinion for PCT/EP2014/051760, dated Jun. 2, 2014.

Rudakova et al., "Comparative analysis of esterase activities of human, mouse and rat blood," Bulletin of Experimental Biology and Medicine 2011; 152(1): 73-75.

Serra S.C. et al, "Hyperpolarized 13C-labelled anhydrides as DNP precursors of metabolic MRI agents," Contrast Media & Molecular Imaging 2012; 7(5): 469-477, XP055045079, ISSN:1555-4309, DOI:10.1002/cmmi.1474.

Schroeder M.A. et al., "Measuring intracellular pH in the heart using hyperpolarized carbon dioxide and bicarbonate: a 13C and 31P magnetic resonance spectroscopy study," Cardiovasc Res 2010; 86:82-91.

Talwar S., "The expression of human carboxylesterases in normal tissues and cancer cell lines," Master thesis, University of Southern California 2008; pp. 1-33.

Yan B. et al., "Rat serum carboxylesterase," Journal of Biological Chem. 1995; 270: 19128-34.

* cited by examiner

HYPERPOLARIZED ESTERS AS METABOLIC MARKERS IN MR

CROSS-REFERENCE TO RELATED APPLICATIONS

This application is the national stage application of corresponding international application number PCT/EP2014/051760, filed Jan. 30, 2014, which claims priority to and the benefit of European application no. 13153469.5, filed Jan. 31, 2013, all of which are hereby incorporated by reference in their entirety.

FIELD OF THE INVENTION

The invention relates to the field of Magnetic Resonance (MR), in particular to a method of $^{13}$C-MR investigation using a diagnostic medium comprising hyperpolarized $^{13}$C esters.

BACKGROUND OF THE INVENTION

Magnetic resonance imaging (MRI) is a technique that has become particularly attractive to physicians as images of a patient's body or parts thereof can be obtained in a non-invasive way and without exposing the patient and the medical personnel to a potentially harmful radiation such as X-rays. Because of its high quality images and good spatial and temporal resolution, MRI is a favourable imaging technique for imaging soft tissue and organs. MRI may be carried out with or without MR contrast agents. However, contrast-enhanced MRI usually enables the detection of much smaller tissue changes, which makes it a powerful tool for the detection of early stage tissue changes like, for instance small tumors or metastases.

MRI using hyperpolarized molecules is an emerging technique. WO 9935508 discloses a method of MR investigation of a patient using a hyperpolarized solution of a high $T_1$ agent as MRI contrast agent. The term "hyperpolarization" means enhancing the nuclear polarization of the NMR active nuclei present in the agent, i.e. nuclei with non-zero nuclear spin, preferably $^{13}$C- or $^{15}$N-nuclei, and thereby amplifying the MR signal intensity by a factor of hundred and more. When using a hyperpolarized $^{13}$C- and/or $^{15}$N-enriched high $T_1$ agent, there will be essentially no interference from background signals as the natural abundance of $^{13}$C and/or $^{15}$N is negligible and thus the image contrast will be advantageously high. The main difference between conventional MRI contrast agents and these hyperpolarized high $T_1$ agents is that in the former changes in contrast are caused by affecting the relaxation times of water protons in the body whereas the latter class of agents can be regarded as non-radioactive tracers, as the signal obtained arises solely from the agent. When hyperpolarization is obtained via a microwave assisted transfer between unpaired electrons and the nuclei used as MR probes, the techniques is referred as Dynamic Nuclear Polarization (DNP).

A variety of possible high $T_1$ agents for use as MR imaging agents are disclosed in WO9935508, including non-endogenous and endogenous compounds. As examples of the latter, intermediates in normal metabolic cycles are mentioned which are said to be preferred for imaging metabolic activity. By in vivo imaging of metabolic activity, information of the metabolic status of a tissue may be obtained and said information may for instance be used to discriminate between healthy and diseased tissue.

For example, WO 2009077575 discloses a method of $^{13}$C-MR detection using an imaging medium comprising hyperpolarized $^{13}$C-fumarate, in order to investigate both the citric acid and the urea cycles by detecting $^{13}$C-malate and optionally $^{13}$C-fumarate and/or $^{13}$C-succinate signals. The metabolic profile generated in a preferred embodiment of the method provides information about the metabolic activity of the body and part of the body under examination and said information may be used in a subsequent step for, e.g. identifying diseases. Such a disease is preferably cancer since tumor tissue is usually characterized by an altered metabolic activity. As a technical aspect, if the compounds to be polarized crystallize upon freezing or cooling their solution, a glass-forming additive must be added to the solution.

Dynamic nuclear polarization (DNP) has been applied recently to magnetic resonance spectroscopy (MRS) in solution, where it can be used to produce a large increase in sensitivity. Using this technique, the metabolism of several $^{13}$C-labeled compounds has been observed and used to estimate rate constants for specific enzyme-catalyzed reactions in vitro and in vivo (Day S E, Kettunen M I, Gallagher F A, Hu D E, Lerche M, Wolber J, Gofman K, Ardenkjaer-Larsen J H, Brindle K M. Detecting tumor response to treatment using hyperpolarized $^{13}$C magnetic resonance imaging and spectroscopy. Nat Med 2007; 13:1382-1387; Gallagher F A, Kettunen M I, Hu D E, Jensen P R, Zandt R I, Karlsson M, Gisselsson A, Nelson S K, Witney T H, Bohndiek S E, Hansson G, Peitersen T, Lerche M H, Brindle K M. Production of hyperpolarized [1,4-$^{13}$C$_2$]malate from [1,4-$^{13}$C$_2$]fumarate is a marker of cell necrosis and treatment response in tumors. Proc Natl Acad Sci USA 2009; 106: 19801-19806). Furthermore, for some hyperpolarized $^{13}$C-labeled substrates there is sufficient signal for the spatial distribution of both the substrate and its metabolites to be imaged in vivo. As some of these substrates have already been administered at relatively high concentrations in the clinic, this technique has the potential to be translated into clinical applications. To date, the most studied reactions have been those involving hyperpolarized [1-$^{13}$C]pyruvate: the hyperpolarized label can be exchanged with either endogenous lactate or alanine, or alternatively it can be irreversibly converted to carbon dioxide, which is subsequently converted to bicarbonate in the reaction catalyzed by carbonic anhydrase. These metabolic reactions have been observed in tumors, in cardiac tissue and in the liver (Merritt M E, Harrison C, Storey C, Jeffrey F M, Sherry A D, Malloy C R. Hyperpolarized $^{13}$C allows a direct measure of flux through a single enzyme-catalyzed step by NMR. Proc Natl Acad Sci USA 2007; 104:19773-19777; Schroeder M A, Swietach P, Atherton H J, Gallagher F A, Lee P, Radda G K, Clarke K, Tyler D J. Measuring intracellular pH in the heart using hyperpolarized carbon dioxide and bicarbonate: a $^{13}$C and $^{31}$P MRS study. Cardiovasc Res 2010; 86:82-91; Hu S, Chen A P, Zierhut M L, Bok R, Yen Y F, Schroeder M A, Hurd R E, Nelson S J, Kurhanewicz J, Vigneron D B. In vivo carbon-13 dynamic MRS and MRSI of normal and fasted rat liver with hyperpolarized $^{13}$C-pyruvate. Mol Imaging Biol 2009; 11:399-407).

The use of hyperpolarized $^{13}$C-pyruvate or [$^{13}$C, $^2$H]-lactate is also disclosed in the patent literature, for example in the following patent documents.

EP2052273 discloses a method for detecting cell death comprising administering an imaging medium comprising hyperpolarized $^{13}$C-pyruvate.

US20100178249 discloses an imaging medium containing lactate and hyperpolarized $^{13}$C-pyruvate.

WO2011138269 discloses the use of hyperpolarized [$^{13}$C, $^{2}$H]-lactate to measure LDH activity.

US20110038802 discloses a method for determining alanine transaminase activity using an imaging medium comprising hyperpolarized $^{13}$C-pyruvate.

WO2008143519 discloses MR methods of grading a tumor using an imaging medium comprising hyperpolarized $^{13}$C-pyruvate. The conversion of pyruvate occurs through oxidative decarboxylation.

In the work of Hurd et al. the use of hyperpolarized ethyl [1-$^{13}$C]-pyruvate (EP) is proposed as an alternative approach to hyperpolarized [1-$^{13}$C]-pyruvate in MR metabolic imaging for neurologic applications, where the blood-brain transport of pyruvate may be a limiting factor (Hurd R E, Yen Y, Mayer D, Chen A, Wilson D, Kohler S, Bok R, Vigneron D, Kurhanewicz J, Tropp J, Spielman D, Pfefferbaum A. Metabolic imaging in the anesthetized rat brain using hyperpolarized [1-$^{13}$C]-pyruvate and ethyl [1-$^{13}$C]-pyruvate. Magn Reson Med. 2010; 63(5): 1137-1143). The authors of the work demonstrate the rapid and preferential ethyl [1-$^{13}$C]-pyruvate uptake into brain and thus suggest the use of hyperpolarized EP for the study of neurodegenerative diseases; the general strategy of using esters for rapid and efficient delivery of agents across the blood-brain barrier is also suggested.

The use of a hyperpolarized ethyl ester is also shown in the work of Brindle et al. (Clive Kennedy B W, Kettunen M I, Hu D, Bohndiek S E, Brindle K M. Detection of hyperpolarized $^{13}$C labelled ketone bodies in vivo. Proc. Intl. Soc. Mag. Reson. Med. 20 (2012)), where ethyl [1,3-$^{13}$C$_2$]-acetoacetate (EAcAc) is injected in non-tumor and tumor bearing mice in order to probe ketone body metabolism in vivo. EAcAc is shown to be rapidly converted into acetoacetate; however, the authors suggest said conversion to take place in the blood due to a non-specific esterase activity, therefore the use of EAcAc to probe ketone metabolism in vivo is disregarded.

Recently, other endogenous molecules have been successfully hyperpolarized: tumor pH has been measured in vivo from the relative concentrations of $^{13}$C-labeled bicarbonate and carbon dioxide following the injection of hyperpolarized $^{13}$C-labeled bicarbonate (Gallagher F A, Kettunen M I, Day S E, Hu D E, Ardenkjaer-Larsen J H, Zandt R, Jensen P R, Karlsson M, Gofman K, Lerche M H, Brindle K M. Magnetic resonance imaging of pH in vivo using hyperpolarized $^{13}$C-labelled bicarbonate. Nature 2008; 453:940-943); elevated levels of hyperpolarized malate have been demonstrated in necrotic tumor tissue in vivo following the injection of hyperpolarized $^{13}$C-labeled fumarate (Gallagher F A, Kettunen M I, Hu D E, Jensen P R, Zandt R I, Karlsson M, Gisselsson A, Nelson S K, Witney T H, Bohndiek S E, Hansson G, Peitersen T, Lerche M H, Brindle K M. Production of hyperpolarized [1,4-$^{13}$C$_2$]malate from [1,4-$^{13}$C$_2$] fumarate is a marker of cell necrosis and treatment response in tumors. Proc Natl Acad Sci USA 2009; 106:19801-19806); the metabolism of glutamine to glutamate, catalyzed by the mitochondrial enzyme glutaminase, has been observed following administration of hyperpolarized $^{13}$C-labeled glutamine to cells in vitro (Gallagher F A, Kettunen M I, Day S E, Lerche M, Brindle K M. $^{13}$C MR spectroscopy measurements of glutaminase activity in human hepatocellular carcinoma cells using hyperpolarized $^{13}$C-labeled glutamine. Magn Reson Med 2008; 60:253-257); the organ-specific metabolism of hyperpolarized $^{13}$C-labeled acetate to acetyl-CoA and acetyl carnitine has been observed in vivo (Jensen P R, Peitersen T, Karlsson M, In't Zandt R, Gisselsson A, Hansson G, Meier S, Lerche M H. Tissue-specific short chain fatty acid metabolism and slow metabolic recovery after ischemia from hyperpolarized NMR in vivo. J Biol Chem 2009; 284:36077-36082), and the metabolism of branched chain amino acids has been observed in tumors following the addition of hyperpolarized $^{13}$C-labeled α-ketoisocaproate (Karlsson M, Jensen P R, In't Zandt R, Gisselsson A, Hansson G, Duus J O, Meier S, Lerche M H. Imaging of branched chain amino acid metabolism in tumors with hyperpolarized $^{13}$C ketoisocaproate. Int J Cancer 2010; 127:729-736.10).

Although its etiology is lacking, cancer is well characterized phenomenological as a molecular disease. Different kinds of cancers may have very different biochemical forms, however they can share general molecular features. Early diagnosis of cancer continues to be given large attention since diagnosis at an early stage often increases the chances of a successful treatment. In fact, early diagnosing cancer and ensuring access to optimum treatment can lead to significant improvements in survival.

Early diagnosing of cancer could be achieved by taking advantage of a general molecular feature shared by different types of cancer cells and whose alteration in cancer can be early detected.

Carboxylesterases (CE, EC 3.1.1.1) are a family of enzymes catalysing the chemical conversion of an ester in an acid and an alcohol. A general reaction scheme is shown above:

Carboxylesterases are ubiquitously expressed in mammalian tissues. The many CE isoforms have been classified into 5 super families (CE 1-5) based on amino acid homologies. The CE1 enzymes are mainly localized to the liver, however they are also expressed in most other tissue types. A rat specific CE1 isoform is secreted from the liver to the blood in rats and mice and this iso-enzyme is correlated to a high level of hydrolase activity detected in rodents compared to humans (Yan, B. Dongfang Y., Bullock, P., Parkinson, A., Rat serum carboxylesterases, 1995, *JBC*, 32 (270): 19128-34; Rudakova, E V., Botneva N P., Makhaeva, G F. Comparative analysis of esterase activities of human, mouse and rat blood, 2011, *Bulletin of experimental biology and medicine,* 152(1): 73-75). The other important isoform is the CE2 family, which is also expressed in the human liver (approx. 4 times less than CE1) as well as in most other tissues to a higher degree than CE1 (Talvar, S. The expression of human carboxylesterases in normal tissues and cancer cell lines (2008), Master thesis).

The expression of carboxylesterases decreases in cancer in both animal and human tissue. In particular, in hepatoma cells a 4 times decrease in the expression of carboxyl esterase has been measured compared to normal hepatocytes. Dependent on the isoform the expression is reported to be approx. 1.5-4 times higher in normal tissue than in the corresponding malignant tissue (Talvar, 2008).

A number of studies have been reported on carboxylesterases in cancer cells.

The expression of carboxylesterase was reported as detectable in human cancer cells (HEPG2) and approx. 3-4 times lower than the expression of carboxyl esterase in normal human liver (hepatocytes) (Talvar, 2008). A patient study on non-tumor and tumor tissues from liver cancer (HCC) patients showed an almost 3 times decrease in the expression of carboxyl esterase in the tumor tissue (Na, K. et al., Human plasma carboxylesterase 1, a novel serologic biomarker candidate for hepatocellular carcinoma (2009), Proteomics, 9: 3989-99).

Another study showed that the carboxylesterase activity was significantly lower in colon cancer xenografts compared to the corresponding normal colon tissue in mice (Jansen et al., CPT-11 in human colon cancer cell lines and xenografts: characterization of cellular sensitivity determinants, 1997, Int. J. Cancer 70:335-40.)

A study has been reported on lung cancer patients where carboxylesterase activity is correlated to esterase expression in healthy and cancer lung tissue. In this study, they find that the activity correlates well with the expression, which is shown to be approx. 1.5 times higher in healthy tissue (Liewald F. et al, Intracellular pH, esterase activity and DNA measurements of human lung carcinomas by flow cytometry. 1990, Cytometry, 11: 341-48)

WO2012102773 discloses a method for the diagnosis and treatment of cancer, in particular breast cancer, by measuring the activity of the enzyme PMPMEase (human carboxylesterase 1). Said activity is measured in a biological sample by assaying the enzyme expression or enzymatic activity, in the last case through the measurement of the consumption of a substrate or the production of a product. It is only generally stated that the enzyme assay can be performed in vivo.

U.S. Pat. No. 8,198,038 discloses a screening method to distinguish healthy human beings from those with human liver cancer (hepatocellular carcinoma; HCC) comprising the steps of collecting human blood and detecting the presence of human liver carboxylesterase 1 (hCE1) in the plasma, wherein the level of hCE1 protein is increased more in the plasma of patients with HCC than in the plasma of healthy patients.

WO2013/006520 discloses a method of metabolic imaging by administering hyperpolarized dialkyl $^{13}$C succinate and detecting the respective hyperpolarized metabolic products. As discussed in the application, the detected metabolites peaks in the $^{13}$C MRS spectra correspond in particular to the respective metabolic products of the Krebs tricarboxylic acid cycle ("TCA cycle"), i.e. succinate, aspartate, malate and fumarate. On the other side, the primary metabolic product of the esterase reaction on dialkyl $^{13}$C succinate (i.e. the monoalkyl $^{13}$C succinate) is not detected by the method illustrated in the application.

In view of the above, there is still the need of a method for specifically distinguish tumor tissue from healthy tissue, in particular by detecting in vivo features shared by different cancer cells.

SUMMARY OF THE INVENTION

It has now been found that the conversion of a hyperpolarized $^{13}$C ester in its corresponding primary hyperpolarized metabolic products catalysed by carboxylesterase in cancer tissues gives rise to signals which are different from those in healthy tissues. Therefore, said difference between the signals in tumor and non-tumor tissues of said hyperpolarized $^{13}$C ester may be useful in the diagnosis of cancer.

Within the context of cancer diagnosis, said difference in the signals of a hyperpolarized $^{13}$C ester metabolized by a carboxylesterase may be used for detecting the presence of a tumor, for evaluating the efficacy of an anti-cancer therapy and/or for determining a time evolution of a tumor.

Therefore, an aspect of the present invention relates to a $^{13}$C ester of monocarboxylic acid or $^{13}$C diester of ($C_1$-$C_7$) dicarboxylic acid for use in $^{13}$C-MR investigation of a tumor, wherein signals of a corresponding primary hyperpolarized metabolic product of a carboxylesterase conversion of said ester are detected.

Preferably the monocarboxylic acid is a ($C_1$-$C_7$) carboxylic acid.

More preferably, the mono- or dicarboxylic acid is a ($C_3$-$C_6$) carboxylic acid and even more preferably a $C_4$ carboxylic acid.

Another aspect of the invention relates to a method of $^{13}$C-MR investigation of tumor using an imaging medium comprising a hyperpolarized $^{13}$C ester, wherein signals of the corresponding hyperpolarized metabolic product of the carboxylesterase conversion are detected.

In the hyperpolarized ester molecule, the $^{13}$C carbon atom(s) may be part of the molecular moiety of the acid, of the alcohol or both. Therefore, the detected metabolic product may be the corresponding acid, the corresponding alcohol or both. Preferably, the $^{13}$C carbon atom(s) is(are) in the acid moiety, more preferably at least the carbon of the carboxylic group is a $^{13}$C carbon atom. Depending on the specific pKa of the carboxylic acid, the acid can be more or less dissociated; the detected product at the physiological pH can thus be either the non-dissociated acid form or the corresponding carboxylate anion. Accordingly, in the following of the specification, the term "acid (or acidic) metabolite (or product)" will include both dissociated and non-dissociated forms, unless differently specified.

In a preferred embodiment of the invention the hyperpolarized ester is a ($C_1$-$C_4$)alkyl ester, more preferably an ethyl ester.

In another preferred embodiment of the invention, said hyperpolarized $^{13}$C ester is an ester of a monocarboxylic acid, preferably a ($C_1$-$C_4$)alkyl ester, more preferably an ethyl ester and even more preferably it is ethyl acetoacetate.

The detected metabolite is preferably the respective acid metabolite, more preferably the carboxylate anion and even more preferably the acetoacetate anion.

In an embodiment of the invention, a first signal obtained from a region of interest is compared with a second signal (typically a signal derived from a reference sample, e.g. a signal obtained from a corresponding non-tumor/healthy tissue); said comparison is useful to determine a difference between tumor and non-tumor tissue, and more in particular can be used to provide a localization of a tumor.

Furthermore, when a first signal obtained from a region of interest comprising a tumor tissue is compared with a second signal obtained from the same region of interest at an earlier time, the comparison between said first and said second signal can provide information about the grade of time evolution, which can also be an indication of aggressiveness, of the tumor and/or the efficacy of a therapy when treating said tumor by (immune)pharmacological and/or surgical and/or radio therapy.

In a preferred embodiment, said first signal is the ratio between the signal of the primary metabolic product of the carboxylesterase conversion and the signal of the administered substrate (the hyperpolarized $^{13}$C ester) detected in the region of interest.

Another aspect of the invention is the above method of $^{13}$C-MR investigation wherein said signals are used to generate a metabolic profile, based on the metabolic carboxylesterase conversion of a $^{13}$C ester into the corresponding hyperpolarized primary metabolic product, wherein said metabolic profile is useful in detecting or providing indication of a tumor.

In an embodiment of the invention, said metabolic profile is determined in a region of interest (where the presence of a tumor tissue is known or suspected) and compared with a metabolic profile of reference (e.g. relative to a corresponding non-tumor tissue, typically a healthy tissue in the close proximity of the tumor tissue).

Another aspect of the present invention is a method for operating an MRI system comprising the steps of:
a. submitting a subject who is affected or suspected to be affected by a tumor, who has been positioned in an MRI system and treated with a hyperpolarized $^{13}C$ ester, and wherein said hyperpolarized $^{13}C$ ester has been metabolically converted into the corresponding hyperpolarized metabolic product of the carboxylesterase conversion, to a radiation having a frequency selected to excite nuclear spin transitions in $^{13}C$ nuclei; and
b. recording an MR signal from said excited nuclei;
c. comparing a first MR signal deriving from a region of interest comprising said tumor or said suspected tumor with a second MR signal deriving from said subject or from a sample taken from said subject.

In an embodiment of the invention, said second signal is an MR-signal deriving from a non-tumor tissue of said subject. In another embodiment of the invention, said second signal is an MR-signal which has been detected from the region of interest, at an earlier time with respect to the first signal.

Another aspect of the invention is the above method further comprising the steps of:
d. determining a difference between said first signal and second signal;
e. comparing said difference of step d) with a reference value, to produce a deviation value; and
f. determining if the deviation value is, in absolute value, higher than a predetermined value.

Another aspect of the present invention is the above method, wherein said second signal is determined on a non-tumor tissue, further comprising the step of:
g. providing an indication of possible tumor affection in case the deviation value is in absolute value higher than said predetermined value.

Another aspect of the present invention is the above method for operating an MRI system comprising steps a) to f), wherein said second signal is determined in the region of interest, at an earlier moment in time with respect to the first signal, and optionally stored in the system, said method further comprising the step of:
g'. providing an indication of tumor variation in case the deviation is in absolute value higher than said predetermined value.

Another aspect of the present invention is the above method for operating an MRI system comprising steps a) to f), wherein said subject has undergone an anti-tumor treatment and wherein said second signal is determined in the region of interest, at an earlier moment in time with respect to said first signal, and optionally stored in the system, said method further comprising the step of:
g". providing an indication of efficacy of said treatment if this deviation is in absolute value higher than a predetermined value.

In a preferred embodiment, said second signal is determined before, after or at the beginning of the treatment, wherein the effective time of detection of said second signal will be decided by the person skilled in the art, according to patient's conditions, kind of treatment, degree of severity of the disease and any other clinical parameter within the general knowledge on the matter. Examples of the time of determination of said second signal are few days, e.g. 1 to 5, one or more weeks, one or more months.

The present invention provides the advantages of making available an imaging medium comprising a hyperpolarized $^{13}C$ ester, which can be used in MRI technique for the diagnosis of tumors with a selective grade of distinction between tumor and non-tumor tissue.

A further advantage is represented by the possibility of taking different registrations of the MR signals of the hyperpolarized $^{13}C$ ester in a tumor tissue, while an antitumor therapy is administered and to monitor the progress of the therapy.

A further advantage is represented by the possibility of detecting aggressive forms of tumors by monitoring the development of the formation of the corresponding $^{13}C$ hyperpolarized metabolic product of the carboxylesterase conversion in a tumor tissue.

These and other aspects of the present invention and advantages will be now disclosed in detail in the following description even by means of Figures and Examples.

DETAILED DESCRIPTION OF THE INVENTION

Within the scopes of the present invention, the term MRI means Imaging (typically for diagnostic purposes) by means of Magnetic Resonance (MR) as commonly intended in the state of the art and for example disclosed in WO200977575 and the references cited therein.

Within the scopes of the present invention, the "imaging medium" and "contrast agent" are used synonymously as commonly intended in the state of the art and for example disclosed in WO200977575 and the references cited therein.

Within the scopes of the present invention, the terms "hyperpolarization", "hyperpolarized" or similar mean enhancing the nuclear polarization of NMR active nuclei present in the high $T_1$ agent as commonly intended in the state of the art and for example disclosed in WO200977575 and the references cited therein.

Within the scopes of the present invention, the term Dynamic Nuclear Polarization (DNP) is a technique in Magnetic Resonance Imaging as commonly intended in the state of the art and for example disclosed in WO200977575 and the references cited therein.

Within the meaning of the present invention, the term "hyperpolarized" means the nuclear spin polarization of a compound higher than thermal equilibrium.

Within the scope of the present invention "MRI system" means apparatus, equipment and all features and accessories useful for performing MR experiments, in particular for diagnostic purposes.

Within the scope of the present invention the expression "primary hyperpolarized metabolic product" referred to the enzymatic conversion of a hyperpolarized $^{13}$C ester of the invention means the metabolic product directly obtained by the enzymatic carboxylesterase conversion of the starting hyperpolarized ester compound. Thus, in case the starting compound is an ester of a monocarboxylic acid, the primary metabolic products of the carboxylesterase conversion are the respective monocarboxylic acid and alcohol forming the ester; in the case the starting compound is a diester of a dicarboxylic acid, the primary metabolic products are the respective monoester of the dicarboxylic acid and the alcohol forming the ester.

The hyperpolarized $^{13}$C ester may be prepared by Dynamic Nuclear Polarization (DNP), which is a known method disclosed, for example, in WO9935508, and in particular in WO2011124672.

The activity of the carboxylesterase isoforms is highly substrate dependent. In general substrates with a smaller alcohol group than acid group are reported to have higher affinity for the carboxylesterase isoform CE1 and the reverse class of substrates with larger alcohol groups than acid groups will have higher affinity for the CE2 enzyme (Imai, T. Human Carboxylesterase Isozymes: Catalytic Properties and Rational Drug Design, (2006) Drug Metab. Pharmacokinet 21(3): 173-85.).

The terms ($C_1$-$C_7$), ($C_2$-$C_6$), $C_4$ etc. when referred to the carboxylic acids in the present application, include carboxylic acids with a straight, branched or cyclic alkyl chain comprising from 2 to 7 (or 3-6 or 4 etc., respectively) carbon atoms (including those of the carboxylic group) which may be variably substituted (e.g. with oxygen, amino group etc.) and may contain single or double bonds in the alkyl chain.

Ethyl esters of ($C_1$-$C_7$), preferably ($C_3$-$C_6$) mono- and di-carboxylic acids are preferred substrates for the CE1 isoform.

Within the group of ethyl monoesters suitable substrates are within the class of low molecular weight ethyl mono esters, in particular ethyl esters of ($C_2$-$C_6$) carboxylic acids. Particularly preferred substrates are acetoacetate ethyl ester and butyrate ethyl ester.

A more preferred substrate is the monoester ethyl acetoacetate. Ethyl acetoacetate provides the advantage of being effectively hydrolyzed in liver cells, where the CE1 enzyme is highly expressed. Ethyl acetoacetate also provides good chemical and physical properties, as high solubility, high polarization, long T1, sufficient chemical shift separation between substrate and product to detect the hydrolysis product in vivo.

Where alkyl (preferably ethyl) di-esters of $C_1$-$C_7$ dicarboxylic acids are used, only one alkyl-group will be hydrolyzed by carboxylesterase (CE1 in particular) resulting in an acidic mono-alkyl ester and respective alcohol (or ethanol). See e.g. Lobell et al., "Enzyme preparation of Pure Alkalenedicarboxylic acids monoesters: chain-length dependence of porcine liver esterase (PLE)-catalysed hydrolyses", J. Chem Soc. Perkin Trans. I, 1993, pages 1713-1714, showing that esterase activity on di-esters having less than 7 carbon atoms leads exclusively to pure monoester (while for esters of dicarboxylic acids with 8 or more carbon atoms, the metabolite is the diacid). The chemical shift between the di-ester and the mono-ester is sufficient to be able to distinguish the product from the substrate in vivo. Preferred diesters are symmetric diesters, i.e. with the same esterforming alkyl groups, such as succinate diethyl ester and 2-oxoglutarate diethyl ester.

In general, it is preferred to employ carboxylic ester substrates which, upon reaction with carboxylesterase, provide primary metabolic compounds which are endogenous, i.e. which the organism, tissue, or cell undergoing to the method of the invention may independently develop or originate from within. Accordingly, alkyl esters of monocarboxylic acids are preferably used, which are metabolized in respective endogenous acid and alcohol molecules, such as, for instance, ethylacetoacetate (metabolized into ethanol and acetoacetate), ethylbutyrate (ethanol and butyric acid), ethylacetate (ethanol and acetic acid) or ehtylpyroglutamate (ethanol and pyroglutamic acid).

A further advantage of the use of esters of carboxylic acids as substrates in the present invention is that their uptake into cells takes place mainly by diffusion through the cell membrane as they are neutral molecules. Therefore, they are not uptake limited and only the activity of the metabolizing enzyme itself has influence on the amount of hyperpolarized product that is produced. This means that the detected signal in the present invention is highly representative of the activity of the carboxylesterase, thus making said substrates particularly useful as real time molecular contrast agents. On the contrary, substrates like monocarboxylic acids, e.g. pyruvic acid, can suffer the disadvantage of being uptake limited; the signal of their hyperpolarized product may therefore be not representative of the activity of the specific enzyme to be detected.

The method of the present invention is a non-invasive method, which allows a real time metabolic assessment of the carboxylesterase activity in vivo. An image representative of said activity is collected seconds to minutes following intravenous injection of the substrate.

Essentially, the method of operating an MRI system according to the present invention comprises the steps of a) recording an MR signal from the excited nuclei; and b) comparing a first MR signal deriving from the tumor or suspected tumor with a second MR signal deriving from the same subject or from a sample thereof.

In a preferred embodiment of the invention, said first signal deriving from said tumor is lower than said second MR signal.

In an embodiment of the present invention, as shown in steps d-f, above, the MRI apparatus can process said first signal and said second signal by comparing each other, calculating a difference between the two signals and comparing said difference with a reference value; as shown in step g above, if this comparison provides a value which is, in absolute value, higher than a predetermined value, then said MRI apparatus provides an indication of possible tumor affection.

The use of said apparatus for monitoring the response of a subject affected by a tumor to antitumor therapy (step g') or for evaluating the aggressiveness of a tumor (step g") are further aspects of the present invention.

Examples of said tumors are tumors selected from the group consisting of liver, colon, prostate and breast. A most preferred tumor is liver tumor.

According to the present invention, the ester can be exploited as a marker of targeted therapies, where for targeted therapy is intended the targeting of molecules important for the carcinogenesis of the cancer cells.

In carrying out the methods of the present invention, the first signal ($S_1$), the second signal ($S_2$) and the reference value (R), depend on how the methods of the invention are applied.

Typically, in order to have comparable data, the MR signals obtained in the method of the invention are normalized with respect to the corresponding signal of the ester used as substrate.

When the method of the present invention is performed to provide an indication of possible tumor affection, said first signal $S_1$ is the ratio between the integral of the MR line of the hyperpolarized metabolic product of the carboxylesterase conversion and the integral of the MR line of the administered substrate (the hyperpolarized $^{13}C$ ester), detected in the region of interest comprising the alleged tumor, while the second signal $S_2$ is the analogue ratio calculated in non-tumor tissue; the reference value R is either equal to $S_2$ or, in case no signal of the hyperpolarized metabolic product, for example an acidic product, is detected in the healthy tissue under consideration, R is set to 3 times the noise standard deviation divided by the substrate signal in the same volume. Preferably, non-tumor tissue is surrounding the tumor, so that the MR system can provide an accurate imaging of the tumor, which is of great importance for the evaluation of surgical intervention.

The first and second MR signals can be obtained either as single signals or calculated as a mean value of a plurality of respective signals determined (from different voxels) in a selected region of interest ($S_1$) or in a non-tumor tissue ($S_2$).

In an embodiment of the invention, said first signal and said second signal can be directly compared, either as single signals or as mean values of a plurality of signals, to obtain the desired information on the tumor tissue. In an alternative embodiment of the invention, the signals can be used to generate a parametric image and the comparison can be performed by comparing the zones of said image corresponding to the first and said second signal.

According to the present invention, a difference between said first and said second signal is determined. This difference ($S_1-S_2$) is important for the different scopes of the present invention.

This difference is compared with the reference value to produce a value representing the deviation (D) of said difference from said reference value:

$$D=(S_1-S_2)/R.$$

If it is determined that this deviation provides a value which is, in absolute value, higher than a predetermined value, this deviation provides an indication of possible tumor affection, of the efficacy of the antitumor therapy or of tumor aggressiveness, depending on the purpose of the method of the invention.

For instance, in an embodiment of the invention, said predetermined value can be set at 2; accordingly, if the calculated value "D" is equal or higher than 2, this can be indicative of a possible presence of a tumor in the region of interest, of the efficacy of the antitumor therapy or of tumor aggressiveness, depending on the purpose of the method of the invention. Preferably a deviation value D of from 2 to 10 can be indicative of said presence, efficacy or aggressiveness, more preferably a deviation from 2 to 20, even more preferably a deviation from 2 to 40, particularly preferred is a deviation from 2 to 60, maximally preferred is a deviation from 2 to 80, the most preferred is a deviation from 2 to 100 or higher.

In an embodiment of the invention, the method is performed on a subject who is suspected to suffer or suffers from a tumor.

In another embodiment of the present invention, the above method is performed on a subject who is undergoing or has been subjected to an antitumor treatment and the reference value is the signal of the hyperpolarized metabolic product of the carboxylesterase conversion in said region of interest determined before, during or after said treatment. As above, if a deviation D is calculated which is higher, in absolute value, than a predetermined value (e.g. higher than 2, and preferably within the above indicated ranges), this provides an indication of the efficacy of the antitumor treatment.

In some embodiments, the present invention can be used in the field of so-called "personalized medicine", or similarly intended. As explained above, tumor therapy is affected by variations in its efficacy even on the same type of tumor and with the same anticancer therapeutic protocol. Such variations are due to the different individual responses by the patients.

Carrying out the method of the present invention allows monitoring (follow-up) the efficacy of a tumor therapy and, in case, allowing the doctor to fit the therapy to the patient.

Typical metabolic imaging procedures with the esters of the invention in human subjects should be performed at magnetic fields ≥1 T. Field strengths of 1.5 T or higher are preferred since the spectral separation between the injected substrate (ester) and the observed metabolite (acid or alcohol) scales linearly with the intensity of the applied field. The MR scanner should be capable to detect $^{13}C$ signals in addition to 1H and although not always mandatory, surface or endoscopic radiofrequency coils may allow achieving better results in specific organs. For prostate investigation for instance, an endorectal $^{13}C$ is expected to strongly increase the sensitivity of the method with respect to a standard whole body resonator. Being the hyperpolarized signals typically available for a time range in the order of 3 to 5 times the longitudinal relaxation rate of the ester, the total acquisition time for a metabolic MR procedure will not exceed 3 min. Spectroscopic imaging sequences such as Single Voxel Spectroscopy (SVS) or Chemical Shift Imaging (CSI) need to be used in order to separate the signal coming from the substrate from that coming from the hyperpolarized metabolic product. Fast spectroscopic imaging sequences such as EPSI are preferred due to the limited time available for the acquisition.

In order for the method to provide enough sensitivity, ester formulations and dissolution/transport protocols which allow to maintain at least 10% polarization at time of injection are preferred, in particular for in vivo applications. Preferably, at least of about 20% polarization is maintained, more preferably at least of about 30% polarization is maintained, even more preferably at least of about 60% polarization is maintained, most preferably at least of about 80% polarization is maintained.

The present invention will be further illustrated by the following examples.

EXAMPLES

Where not otherwise specified, chemicals and reagents used in the following examples are commercially available or can be prepared according to methods well-known in the art.

Example 1—General Carboxylesterase Activity in Cancer Cells

General carboxylesterase activity was determined spectrophotometrically using the carboxylesterase substrate 1-naphthyl acetate (NA) as described previously (Rudakova, 2011). Briefly, sonicated cells were incubated with 1 mM substrate in 150 mM phosphate buffer (pH 7.5), and generation of 1-naphtol was monitored at 322 nm and quantified from its extinction coefficient (2200 M−1 cm−1). The reaction is allowed to take place for 10 min at 30 degrees. The substrate concentration and the temperature are chosen to obtain assay conditions under which the assay shows linear behaviour.

The following is the reaction scheme for general esterase detection assay:

Cells of different origin (rat hepatoma, Morris; human hepatoma, HepG2; human prostate carcinoma, PC-3; human breast carcinoma, MCF-7) were harvested and redissolved in phosphate buffer to a concentration of 10 million cells/ml.

The sample composition was as follows: 923 μl phosphate buffer (150 mM pH 7.3)+77 μl NA solution (13 mM in acetone)+100 μl cells in suspension. The absorbance of the samples were compared to reference samples where acetone was added instead of substrate. The esterase activity was calculated using the extinction coefficient $\varepsilon_{322}$=2200 $M^{-1}$ $cm^{-1}$.

Results

Figure 1:
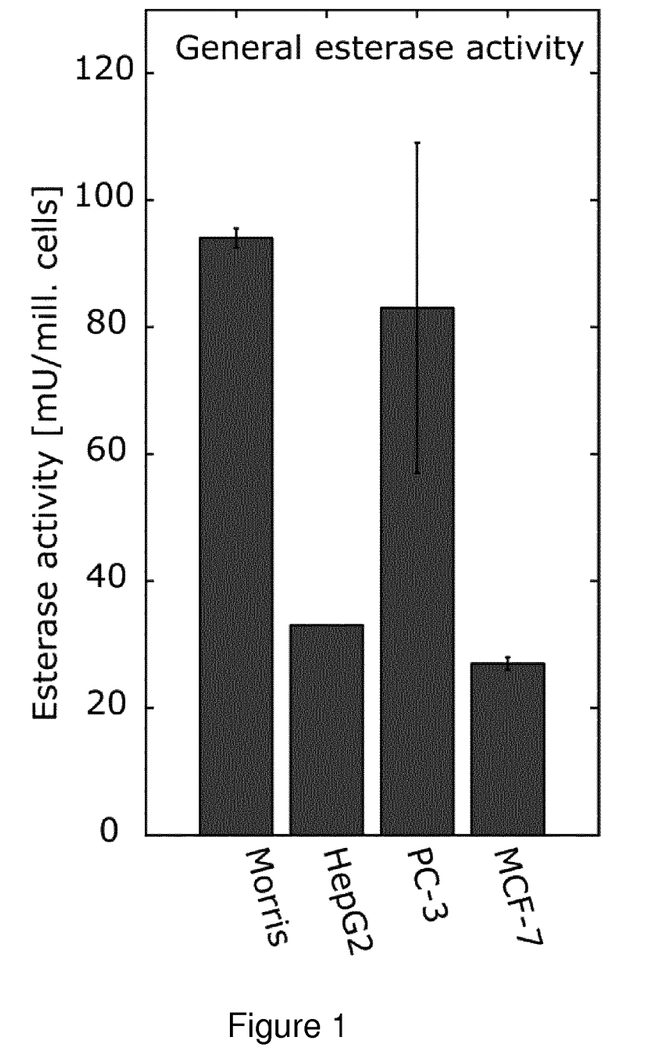
FIG. 1: General carboxylesterase activity measured with NA as substrate in 4 different cancer cell lines (rat hepatoma, Morris; human hepatoma, HepG2; human prostate carcinoma, PC-3; human breast carcinoma, MCF-7).

Since NA is a substrate for both carboxylesterase CE1 and CE2 this example shows that general carboxylesterase activity is found as expected in liver cells but also in prostate and breast cells (FIG. 1).

The capacity of both liver cancer cells (rat as well as human origin) and prostate cancer cells to hydrolyse ethyl acetoacetate in a carboxyl esterase catalyzed reaction is very high with measured activities up to 95 mU/million cells.

Example 2—Carboxylesterase Activities Measured with Hyperpolarized Ethyl [1,3-$^{13}C_2$]-acetoacetate 2.a. Production of Hyperpolarized Ethyl [1,3-$^{13}C_2$]-acetoacetate A) Finland radical, carboxylic acid form (0.85 mg, 0.82 μmol) was dissolved in ethyl [1,3-$^{13}C_2$]-acetoacetate (48 μl, 50.1 mg, 0.378 mmol). To the solution was added a DMSO solution of gadolinium complex [[α1,α4,α7-tris[(phenylmethoxy)methyl]-1,4,7,10-tetraazacyclododecane-1,4,7,10-tetraacetate(4-)]gadolinate(1-)]hydrogen (1.1 mg of a 100 μmol/g solution). The concentration of radical and gadolinium were 17 mM and 2.3 mM respectively.

B) 30 μmol of solution A) was hyperpolarized. The sample was dissolved in 5 ml phosphate buffer (40 mM, pH 7.3). The pH after dissolution was 7.3.

2.b. Carboxylesterase Activities Measured with Hyperpolarized Ethyl [1,3-$^{13}C_2$]-acetoacetate in Rat Liver Cancer Cells (Morris7777) and Human Liver Cancer Cells (HepG2)

A) 10 million cells (either rat liver cancer cells (Morris7777) or human liver cancer cells (HEP-G2)) were harvested and redissolved in 500 ml phosphate buffer (PBS). The cells in suspension were transferred to a 10 mm NMR tube and placed with a connecting tubing in a 14.1 T magnet at 37° C.

B) 2 ml of the dissolved hyperpolarized ethyl [1,3-$^{13}C_2$]-acetoacetate was injected through the connecting line (dead volume 1 ml) resulting in a total substrate concentration of 3.5 mM. A series of 30 degree pulses every 2 s (56 scans in total) was acquired. The acquisition was started just before injection of the hyperpolarized substrate.

Results

Figure 2:
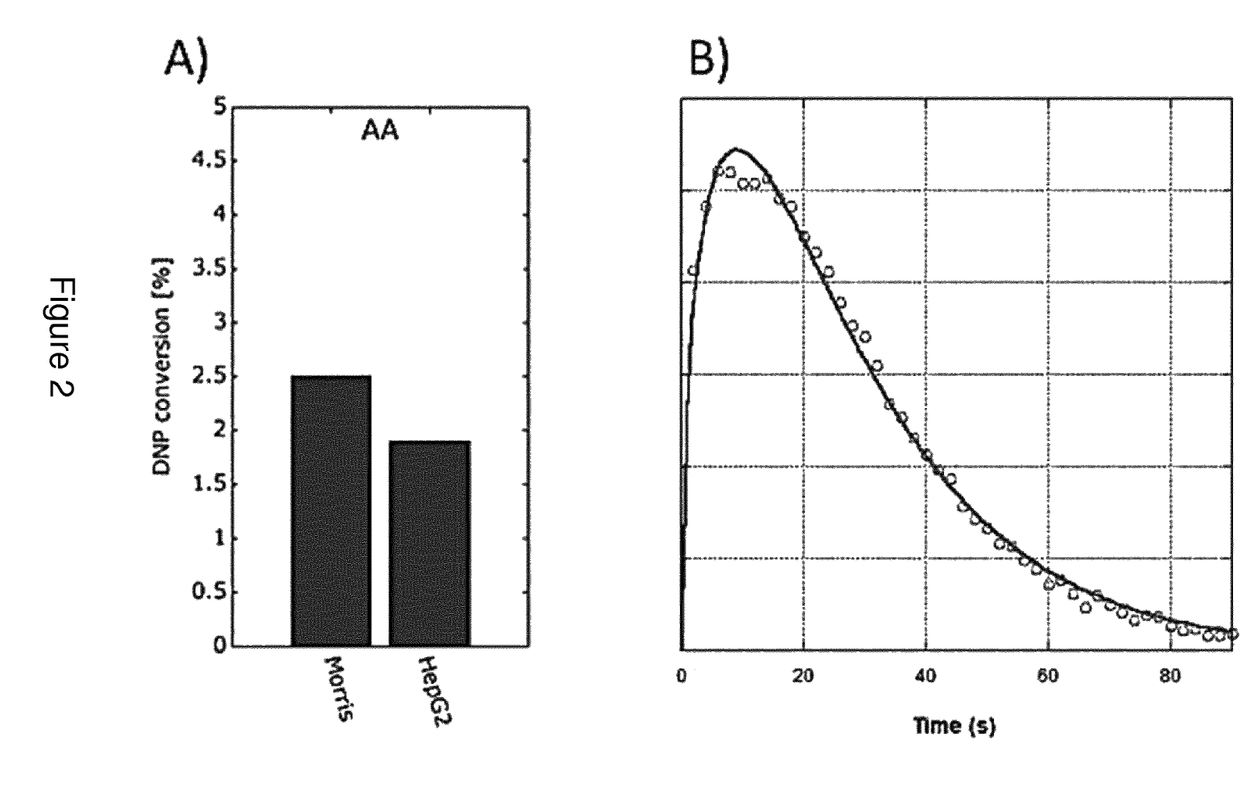
FIG. 2: A) In cell DNP conversion of ethyl $[1,3-^{13}C_2]$-acetoacetate in rat and human liver cancer cells (rat hepatoma, Morris; human hepatoma, HepG2). The DNP experiments are performed with 10 million cells. B) Build-up of the metabolite $[1,3-^{13}C_2]$-acetoacetate anion from injection of ethyl $[1,3-^{13}C_2]$-acetoacetate into whole Morris cells.

An account of produced hyperpolarized 1,3-$^{13}$C-acetoacetate anion in rat and human liver cancer can be seen in FIG. 2.

It can be appreciated from this example that it is possible to follow the build-up of the product, hyperpolarized [1,3-$^{13}$C$_2$] acetoacetate anion resulting from the hydrolysis of hyperpolarized ethyl [1,3-$^{13}$C$_2$]-acetoacetate in whole Morris7777 and whole HepG2 cells.

Figure 3:
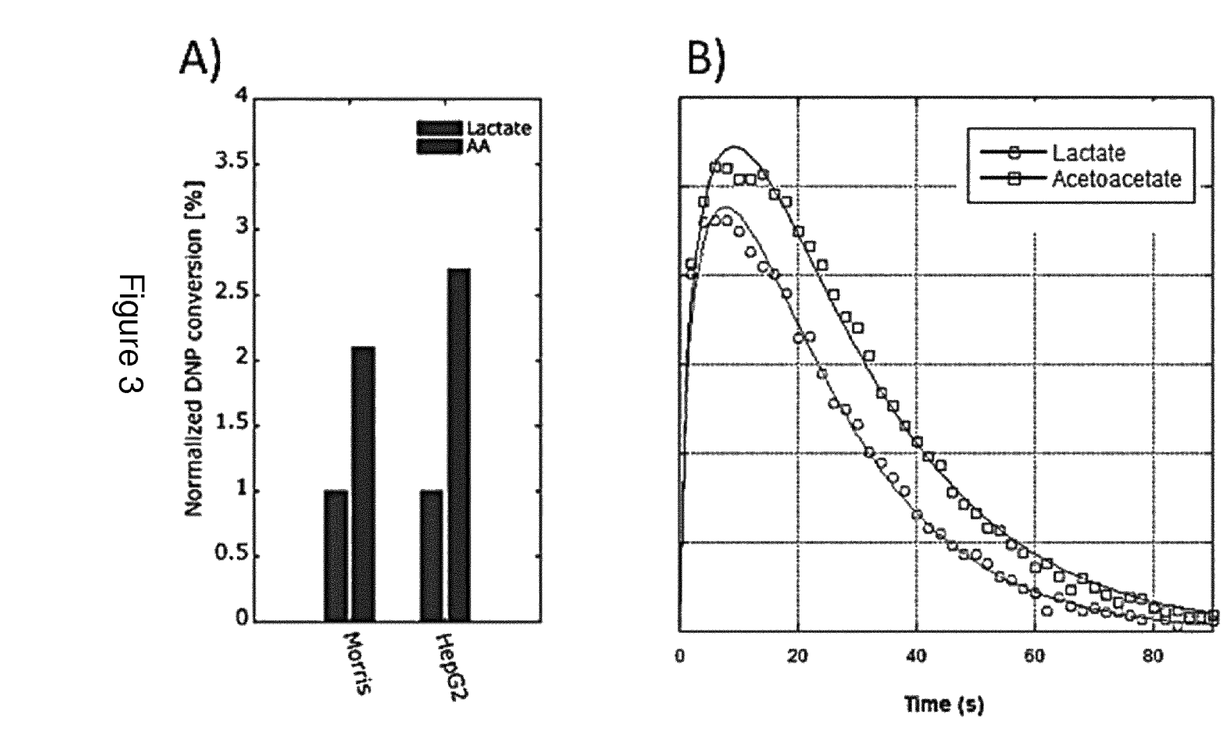
FIG. 3: A) Relative in cell DNP conversion of ethyl $[1,3-^{13}C_2]$-acetoacetate and $[1-^{13}C]$-pyruvate in rat and human liver cancer cells (rat hepatoma, Morris; human hepatoma, HepG2). The DNP experiments are performed with 10 million cells. B) Build-up of the metabolites $[1,3-^{13}C_2]$-acetoacetate anion and $[1-^{13}C]$-lactate anion in whole Morris cells. Only build-up of the signal from acetoacetate anion C1 is represented.

Example 3—Comparison Between Metabolism of Hyperpolarized Ethyl [1,3-$^{13}$C$_2$]-acetoacetate and Hyperpolarized [1-$^{13}$C]-pyruvate in Liver Cancer Cells The experiments are performed with a co-polarization of ethyl [1,3-$^{13}$C$_2$]-acetoacetate and [1-$^{13}$C]-pyruvic acid in equal amounts of compounds (30 μmol) resulting in a concentration of approx. 3.5 mM of each substrate in the experiments. The DNP preparation of ethyl [1,3-$^{13}$C$_2$]-acetoacetate was performed as described in example 2.a. and the DNP preparation of [1-$^{13}$C]-pyruvate was performed as described in WO 2006/011809. The two substrates were co-polarized without mixing the substrates. Following dissolution in 5 ml phosphate buffer (40 mM pH 7.3) with addition of 2.5 μl NaOH to neutralize the pyruvic acid (which is thus converted into the pyruvate anion form), the substrate mixture was injected into 10 million cells in suspension. The experiment was performed as described in Example 2.b. Data are presented as area under the curve of the metabolites divided by the substrate signal in the first spectrum and multiplied by 100 to obtain the unit, DNP conversion is expressed in percentage (FIG. 3).

Results

The amount of signal on [1,3-$^{13}$C$_2$]-acetoaceate anion coming from an addition of the two labelled carbon atoms is approx. twice the signal on [1-$^{13}$C]-lactate anion in a DNP in cell experiment in rat hepatoma Morris cells. This indicates a similar turn-over of the two substrates since differences in polarization levels and T1 relaxation of the substrates are either minor or of little importance under the applied experimental conditions. Similar comparison has been made in human liver cancer cells (HepG2). The relative amounts of hyperpolarized signal on the metabolites, [1-$^{13}$C]-lactate anion and [1,3-$^{13}$C$_2$]-acetoacetate anion is larger in this case, FIG. 3.

Example 4—Concentration Dependent Metabolism of Hyperpolarized Ethyl [1,3-$^{13}$C$_2$]-acetoacetate and Hyperpolarized [1-$^{13}$C]-pyruvate in Rat Cancer Cells All experiments were performed with a co-polarization of ethyl [1,3-$^{13}$C$_2$]-acetoacetate and [1-$^{13}$C-pyruvic] acid in equal amounts of compounds (approx. 10, 30 and 90 μmol) resulting in an experimental concentration of approx. 1, 3.5 and 10 mM of each substrate after dissolving and neutralizing the solid solution as described in Example 3. In all experiments 10 million cells were used. The experimental set-up from Example 2.b was applied. Data are shown as maximum peak intensity of either substrate or metabolite signals.

Results

Figure 4:
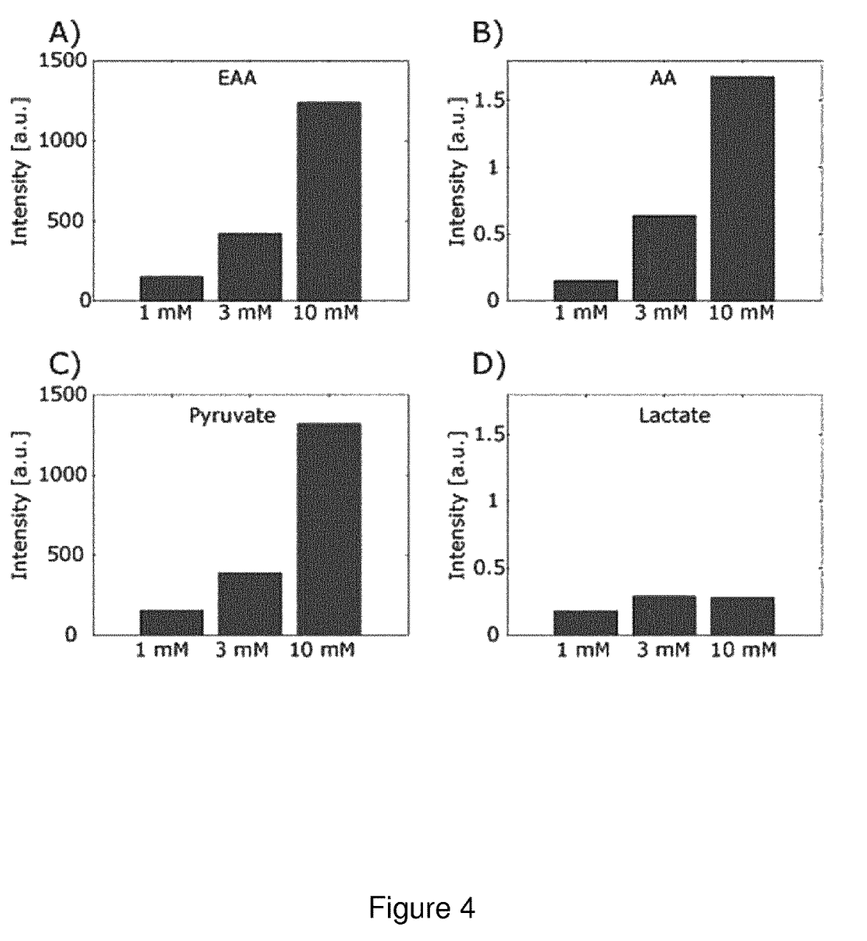
FIG. 4: A) Intensity of the substrate ethyl $[1,3-^{13}C_2]$-acetoacetate with increasing concentration and B) the corresponding change in $[1,3-^{13}C_2]$-acetoacetate anion signal. Figure C) shows intensity of the substrate $[1-^{13}C]$-pyruvate with increasing concentration and figure D) shows the corresponding change in $[1-^{13}C]$-lactate signal.

FIG. 4 shows the corresponding higher substrate signal from ethyl acetoacetate (EAA) and pyruvate with increasing concentration. Likewise the resulting change in measured amount of metabolite ([1,3-$^{13}$C$_2$]-acetoacetate anion (AA) and [1-$^{13}$C]-lactate anion) is shown with increasing substrate concentration. The metabolite signal coming from ethyl acetoacetate increases almost quantitatively with increasing substrate concentration. In contrast, the lactate signal is unchanged going from 3 mM to 10 mM suggesting an uptake limitation or otherwise cellular metabolic limitations when pyruvate is the substrate.

Example 5—Comparison Between Metabolism of Hyperpolarized Ethyl [1,3-$^{13}$C$_2$]-acetoacetate and Hyperpolarized [1-$^{13}$C]-pyruvate in Rat and Human Blood All experiments were performed with a co-polarization of ethyl [1,3-$^{13}$C$_2$]-acetoacetate and [1-$^{13}$C]-pyruvate in equal amounts of compounds (90 μmol) resulting in a concentration of approx. 5 mM of each substrate in the experiments after dissolving and neutralizing the solid solution as described in Example 3. In all experiments 2.5 ml human blood or 2.5 ml rat blood was used. The experimental set-up from Example 2.b was applied. Data are presented as area under the curve of the metabolites divided by the substrate signal in the first spectrum and multiplied by 100 to obtain the unit, DNP conversion in percentage.

Results

Figure 5:
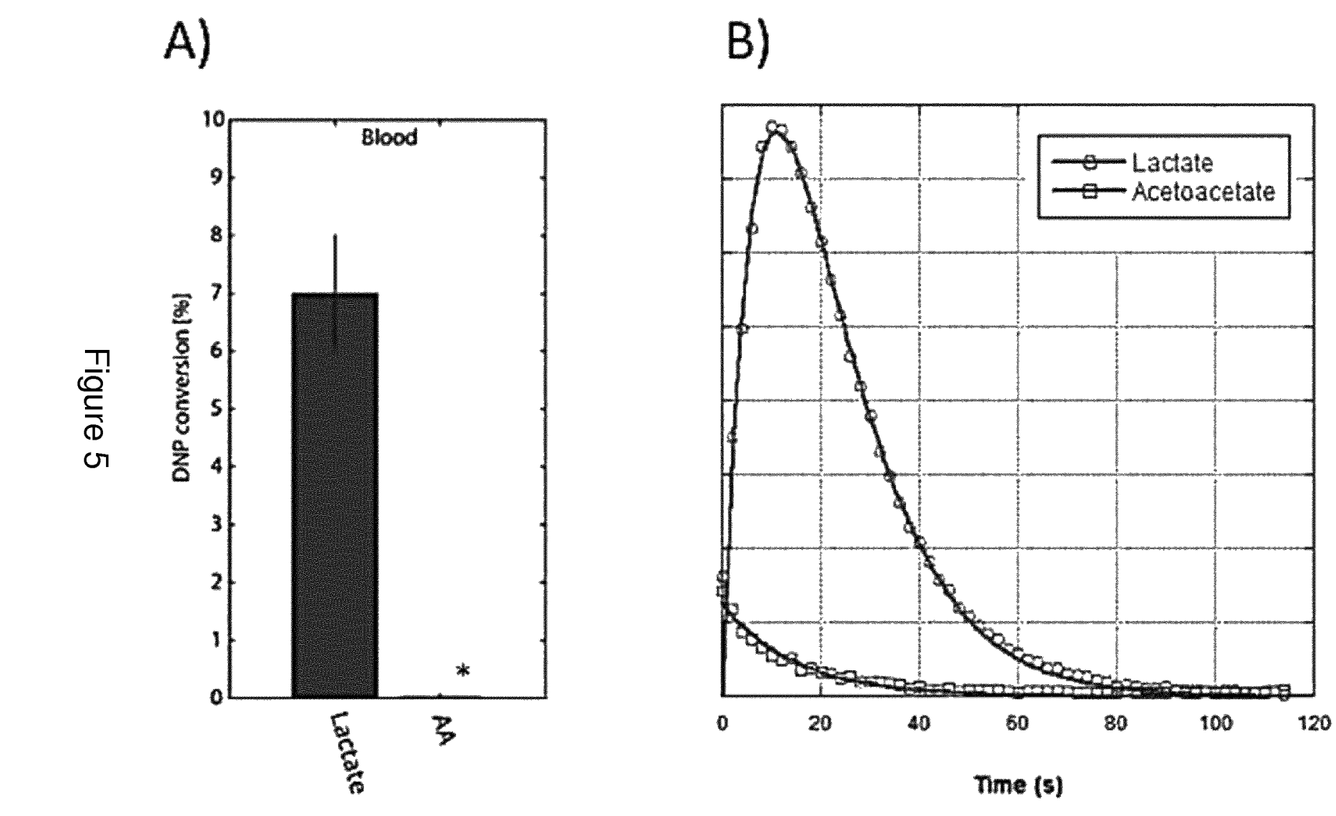
FIG. 5: A) DNP conversion into $[1-^{13}C]$-lactate anion and $[1,3-^{13}C_2]$-acetoacetate anion in percentage of substrate signal (n=3). B) Metabolite build-up of $[1-^{13}C]$-lactate anion compared to that of $[1,3-^{13}C_2]$-acetoacetate anion in human full blood. Since only a decay of the acetoacetate signal can be detected, the hydrolysis of the substrate ester is expected to have taken place during the DNP dissolution procedure.
Figure 6:
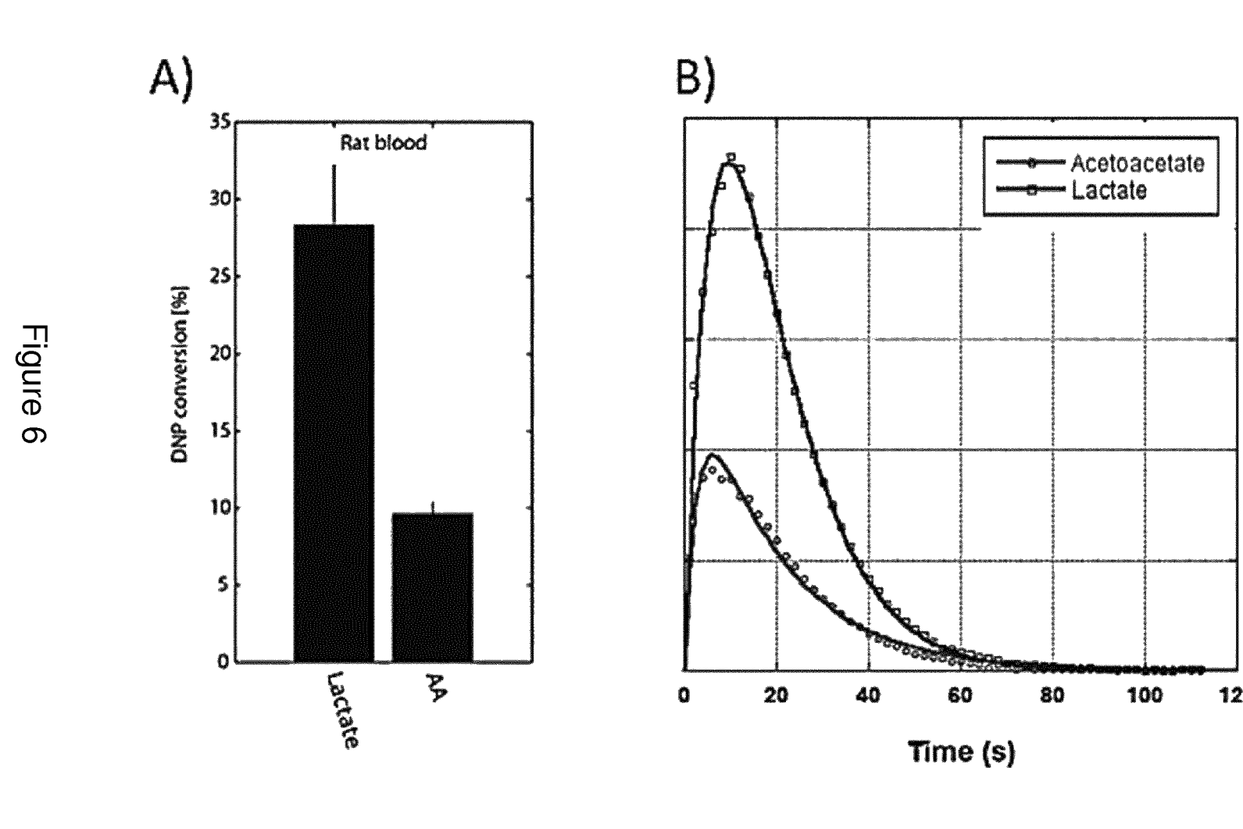
FIG. 6: A) DNP conversion into $[1-^{13}C]$-lactate anion and $[1,3-^{13}C_2]$-acetoacetate anion in percentage of substrate signal (n=3). B) Metabolite build-up of $[1-^{13}C]$-lactate anion compared to that of $[1,3-^{13}C_2]$-acetoacetate anion in rat whole blood.

In FIGS. 5 and 6 the lactate dehydrogenase (LDH) activity in human (FIG. 5) and rat (FIG. 6) full blood is compared to that of carboxyl esterase activity.

Under the experimental conditions applied in these experiments no build-up of metabolite signal could be measured coming from ethyl acetoacetate in the human blood whereas conversion of ethyl acetoacetate is seen in rat blood. The build-up of lactate is significant in both rat and human whole blood and is in both matrixes higher than the conversion of ethyl acetoacetate. No quantitative comparison can be made to the relative conversion in blood to cancer cells due to the differences in cell size and amount of cells in the two different experiments. Although carboxyl esterase is found in low quantities in rat blood and may be found in human blood in even lower quantities the contamination of the measured metabolite signal in tissue by that coming from blood is expected to be insignificant and in all instances less of an issue than what it may be using [1-$^{13}$C]-pyruvate as a substrate.

Example 6—Comparing Carboxyl Esterase Activity on Different Ethyl Esters

The experiments were performed with commercially available CE1 from pig's liver.

The ethyl esters used as substrates are: ethyl acetoacetate (EAA); ethyl acetate (EA); ethyl butyrate (EB); ethyl pyroglutamate (EPG); ethyl pyruvate (EP); diethyl succinate (DES).

Individual samples of the substrates were all made in the following way: 26 μmol was weighted in an eppendorf tube. 550 μl deuterated phosphate buffer (200 mM, pH 7.5) was added and the substrate was brought into solution by whirl mixing. The solution was transferred to a 5 mm NMR tube and inserted in the spectrometer at 37° C. A reference experiment was acquired on the substrate solution without enzyme after which 10 μl of an esterase stock solution (37 U/ml in deuterated phosphate buffer) was added in the top of the tube. The sample was mixed and returned to the spectrometer. A series of thermal 1D 1H NMR experiments were recorded every 5 min for 60 min. The data were analyzed and presented as peak intensity of the product scaled to the peak intensity of the substrate signal in the first spectrum.

Results

Figure 7:
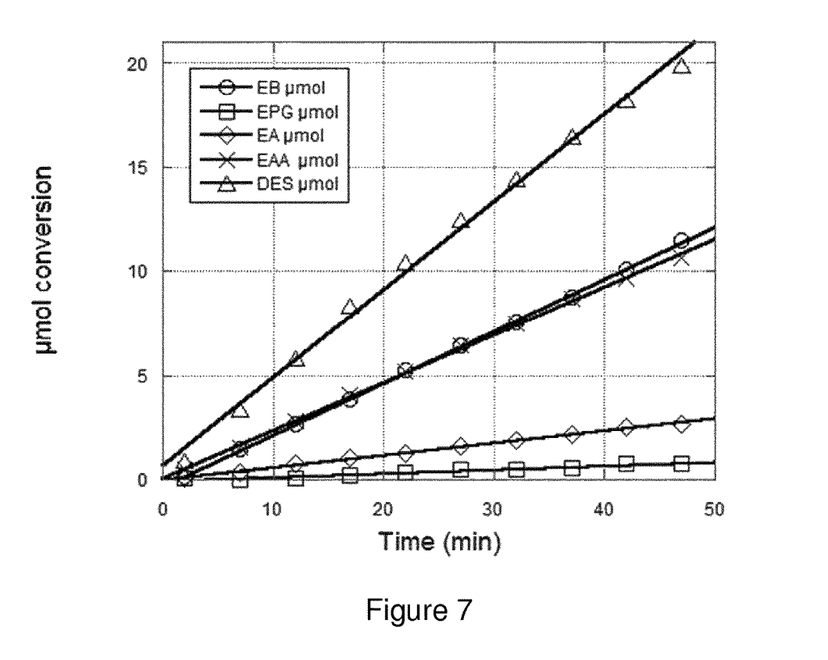
FIG. 7: Different ethyl and diethyl ester conversion rates determined for 5 substrates of an isolated pig liver carboxyl esterase. The included substrates in the comparison are: EAA, Ethyl acetoacetate; EA, ethylacetate; EB, ethylbutyrate; EPG, ethyl pyroglutamate; DES, diethyl succinate.

All of the investigated esters were substrates for CE1, however with very different turnover rates, FIG. 7. The overall fastest converted substrate was diethyl succinate, which was almost a factor of 2 faster converted than ethyl butyrate and ethyl acetoacetate and ten times faster converted than ethyl acetate. In diethyl succinate only one of the ester groups is hydrolyzed; the mono-ester is not a substrate for CE1. Conversion of the ethyl ester of pyroglutamate was barely detectable and no conversion at all could be measured with ethyl pyruvate.

Example 7—Carboxylesterase Activities Measured with Hyperpolarized Ethyl [1,3-$^{13}C_2$]-acetoacetate in vivo in Rat Liver with Implanted Morris7777 Tumor 4 anesthetized Buffalo rats were injected under the hepatic capsula of the liver left lobe with one million McA-RH7777 cells suspended in 0.2 mL of Dulbecco's Modified Eagle's Medium (DMEM) medium.

0.24 mmol of an ethyl [1,3-$^{13}C_2$]-acetoacetate sample made following the description in example 2.a was hyperpolarized. The sample was dissolved in 5 ml TRIS buffer (40 mM, pH 7) added with EDTA 100 mg/l. The pH after dissolution was 7.5.

To each animal an amount of 2.8 ml of the dissolved hyperpolarized ethyl [1,3-$^{13}C_2$]-acetoacetate was injected intravenously at an injection rate of about 0.25 mL/s through a catheter placed in the tail vein of the animal (dead volume 0.3 ml) resulting in a total administered dose of 0.4 mmol/kg. Chemical Shift Imaging (CSI) maps were acquired on a approx. 8 mm coronal slice placed in the abdominal region of the rat. The in plane field of view was set to 40×55 mm² and the corresponding matrix size was 14×14. Remaining acquisition parameters were set as follows: RF flip angle=5°, Repetition Time=105 ms. The acquisition was started at the end of the injection of the ethyl [1,3-$^{13}C_2$]-acetoacetate and ended 20 s later.

Results

Figure 8:
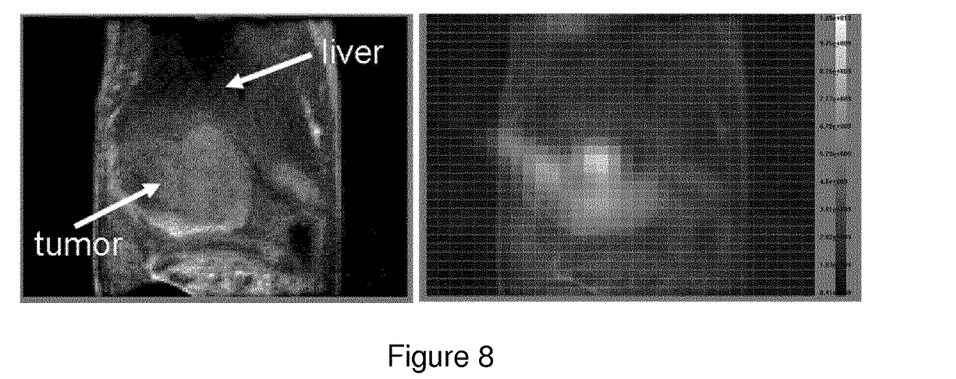
FIG. 8: Coronal 1H anatomical MR image and $^{13}$C CSI map of the 1-$^{13}$C peak of ethyl acetoacetate. Significant amount of Ethyl acetoacetate is found in the tumour mass only, since in the healthy liver, during the 20 s acquisition time, it is almost completely converted towards its hyperpolarized metabolic product.
Figure 9:
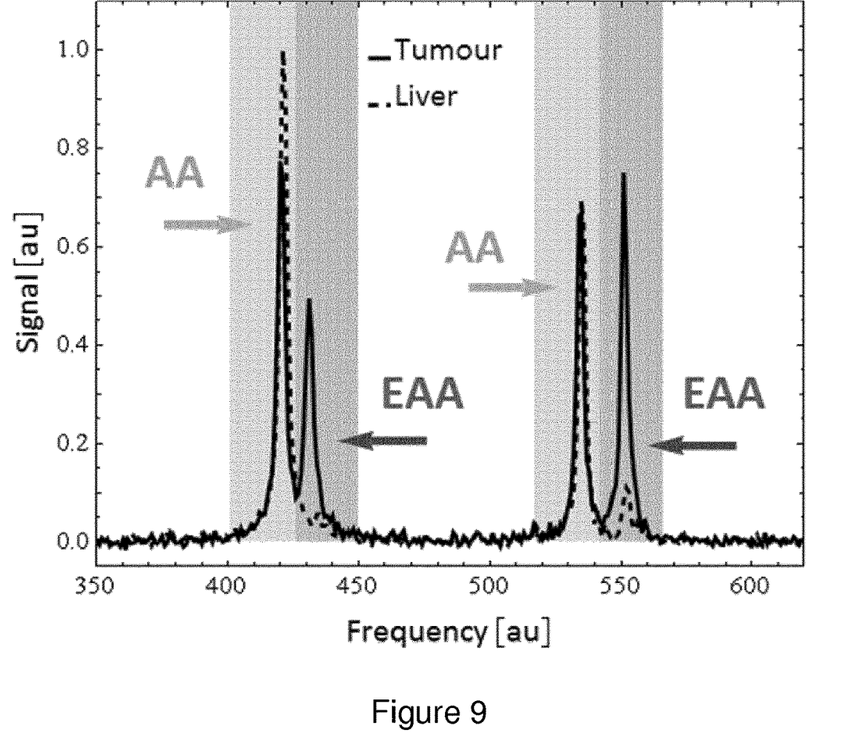
FIG. 9: $^{13}$C spectra of tumour and liver tissues after administration of ethyl [1,3-$^{13}$C$_2$]-acetoacetate obtained as averages of CSI individual spectra over ROIs placed on the tumour mass (solid line) and on the healthy hepatic tissue (dotted line). Peaks from 1-$^{13}$C and 3-$^{13}$C of acetoacetate anion (AA) and ethyl acetoacetate (EAA) are clearly visible.
Figure 10:
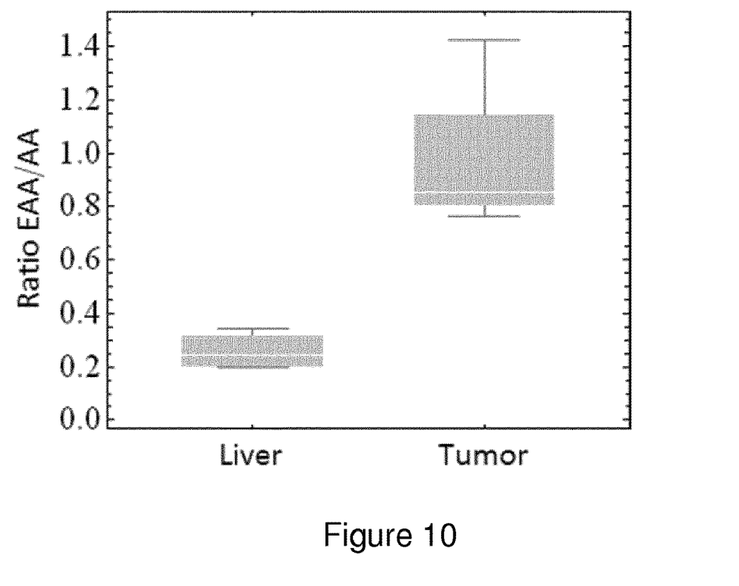
FIG. 10: Ratio between the areas of EAA and AA peaks in the voxel-averaged $^{13}$C CSI spectra from tumour and healthy liver ROIs. The Whisker box plot shows the distribution of data acquired on n=4 Morris hepatocellular carcinoma bearing rats. A significant difference in the EAA/AA ratio between the two tissues is observed, pointing out a dissimilar efficiency of the enzymatic conversion of EAA.

In FIG. 8, a CSI map of the distribution of ethyl acetoacetate on a representative Morris hepatocellular carcinoma bearing rat is reported. The ethyl acetoacetate is mainly observed in the tumour mass. FIG. 9 shows the corresponding $^{13}C$ spectra averaged over Regions of Interest (ROIs) placed on the tumour mass and on the liver. FIG. 10 shows the data distribution (over 4 rats) of the ratio between the peak area of ethyl acetoacetate and acetoacetate anion in liver and tumour calculated from voxel-averaged spectra as those displayed in FIG. 9.

All the experimental observations indicate faster conversion of ethyl [1,3-$^{13}C_2$]-acetoacetate in normal hepatocytes with respect to cancer tissue. The existence of a different metabolic activity between healthy and diseased tissue allows for the diagnosis of the tumour mass in a hepatocellular carcinoma rat model by means of a CSI acquisition after administration of hyperpolarized ethyl [1,3-$^{13}C_2$]-acetoacetate.

Example 8—In vivo $^{13}C$ MRS Data Illustrating the Conversion of Ethyl [1,3-$^{13}C_2$]-acetoacetate in Healthy Liver and Liver Cancer One million McA-RH7777 cells have been suspended in 0.2 mL of Dulbecco's Modified Eagle's Medium (DMEM) and injected under the hepatic capsula of the liver left lobe of anesthetized Buffalo rats.

0.24 mmol of ethyl [1,3-$^{13}C_2$]-acetoacetate sample made following the description in example 2.a were hyperpolarized. The sample was dissolved in 5 ml TRIS buffer (40 mM, pH 7) added with EDTA 100 mg/l. The pH after dissolution was 7.5.

An amount of 2.8 ml of the dissolved hyperpolarized ethyl [1,3-$^{13}C_2$]-acetoacetate was injected intravenously at an injection rate of about 0.25 mL/s through a catheter placed in the tail vein of the animal (dead volume 0.3 ml) resulting in a total administered dose of 0.4 mmol/kg and a substrate concentration of 48 mM.

A total of 8 animals were used in the study. 4 rats were implanted with the tumour (i.e. tumour group) whereas the remaining animals were used as controls (i.e. liver group) in order to have a comparison between healthy and diseased tissue on the same strain. The metabolic fate of injected ethyl [1,3-$^{13}C_2$]-acetoacetate was followed by means of a localised spectroscopy sequence which allows a selective acquisition of either tumour or healthy liver tissue. Acquisition started just before injecting the hyperpolarized substrate and comprised a series of 64 time-domain points sampled at a rate of 3 s. The applied flip angle was equal to 10 degrees.

Results

Hyperpolarized ethyl [1,3-$^{13}C_2$]-acetoacetate is taken up by both healthy and diseased liver cells and converted into its hyperpolarized metabolite, [1,3-$^{13}C_2$]-acetoacetate anion, on the time scale of the DNP experiment. While the signal of the hyperpolarized substrate is decaying, the signal of its hyperpolarized metabolic product is building up, due to the partial conversion of the hyperpolarized ethyl [1,3-$^{13}C_2$]-acetoacetate into its metabolite, and eventually decaying according to its $T_1$ relaxation rate.

The faster decrease of the hyperpolarized substrate (ethyl [1,3-$^{13}C_2$]-acetoacetate) signal, together with the higher ramping up rate of the metabolite signal observed in healthy liver with respect to cancer tissue (typically≥2) indicates a higher conversion rate in normal liver versus diseased tissue and in turn a greater esterase activity. Therefore, the existence of a different metabolic activity between healthy and diseased tissue can be highlighted through localized dynamical $^{13}C$ spectroscopy after administration of hyperpolarized ethyl [1,3-$^{13}C_2$]-acetoacetate.

The invention claimed is:

1. A method for diagnosing a tumor comprising the steps of:
    a. administering an imaging medium comprising hyperpolarized $^{13}C$ ethyl acetoacetate to a subject affected or suspected to be affected by the tumor or to a first sample taken from the subject, wherein said ethyl acetoacetate is metabolically converted into a corresponding hyperpolarized acetoacetate anion metabolic product of a carboxylesterase conversion,
    submitting the subject or the first sample to a radiation having a frequency selected to excite nuclear spin transitions in $^{13}C$ nuclei;
    b. recording (1) at least one first MR signal from said excited nuclei deriving from a region of interest comprising said tumor or said suspected tumor and (2) at least one second MR signal from said excited nuclei deriving from healthy tissue of said subject or from a second healthy sample taken from said subject;
    c. comparing the at least one first MR signal with the at least one second MR signal;
    d. determining a difference between said first signal and said second signal;
    e. comparing said difference with a reference value, to produce a deviation value;

f. determining if the deviation value is, in absolute value, higher than a predetermined value of from 2 to 100; and g. providing an indication of possible tumor affection where the deviation value is in absolute value higher than said predetermined value.

2. The method according to claim 1, wherein said indication is used to provide a localization of the tumor.

3. The method according to claim 1, wherein said first signal is the ratio between the signal of the hyperpolarized acetoacetate anion metabolic product of the carboxylesterase conversion and the signal of the administered hyperpolarized $^{13}C$ ethyl acetoacetate.

4. The method according to claim 2, wherein said first signal is the ratio between the signal of the hyperpolarized acetoacetate anion metabolic product of the carboxylesterase conversion and the signal of the administered hyperpolarized $^{13}C$ ethyl acetoacetate.

5. The method according to claim 1, wherein the tumor is a liver tumor.

6. A method for determining tumor aggressiveness or efficacy of an anti-tumor therapy in a subject comprising:

a. administering an imaging medium comprising hyperpolarized $^{13}C$ ethyl acetoacetate to a subject affected or suspected to be affected by a tumor or to a first sample taken from the subject wherein said ethyl acetoacetate is metabolically converted into a corresponding hyperpolarized acetoacetate anion metabolic product of a carboxylesterase conversion, b. submitting the subject or the first sample to a radiation having a frequency selected to excite nuclear spin transitions in $^{13}C$ nuclei;

c. recording a first MR signal from said $^{13}C$ excited nuclei from a region of interest comprising said tumor;

d. administering the imaging medium to the subject or a second sample taken from the subject wherein said ethyl acetoacetate is metabolically converted into a corresponding hyperpolarized acetoacetate anion metabolic product of a carboxylesterase conversion;

e. submitting the subject or the second sample to a radiation having a frequency selected to excite nuclear spin transitions in $^{13}C$ nuclei;

f. recording a second MR signal derived from the region of interest comprising said tumor, wherein said second MR signal is recorded at an earlier moment in time with respect to the first MR signal;

g. comparing the first MR signal with the second MR signal;

h. calculating the difference between said first signal and second signal;

i. comparing said difference of step e) with a reference value, to produce a deviation value;

j. comparing the deviation value with a predetermined value of from 2 to 100; and k. providing an indication of tumor variation if the deviation has an absolute value higher than said predetermined value.

7. The method according to claim 6, wherein the first signal is the ratio between the signal of the hyperpolarized acetoacetate anion metabolic product of the carboxylesterase conversion and the signal of the administered hyperpolarized $^{13}C$ ethyl acetoacetate, and wherein the second signal is the ratio between the signal of the hyperpolarized acetoacetate anion metabolic product of the carboxylesterase conversion and the signal of the administered hyperpolarized $^{13}C$ ethyl acetoacetate.

8. The method according to claim 6, wherein said subject has undergone an anti-tumor treatment.

9. The method according to claim 8, wherein said second signal is determined one to five days before, one to five days after, or at the beginning of the treatment.

10. The method according to claim 6, wherein the tumor is a liver tumor.

* * * * *